US006616929B1

(12) United States Patent
Hwong et al.

(10) Patent No.: US 6,616,929 B1
(45) Date of Patent: Sep. 9, 2003

(54) SWINE VESICULAR DISEASE VIRUS EXPRESSION VECTORS

(75) Inventors: Ching-Long Hwong, Taipei (TW); Cheng-Kai Lo, Taipei (TW); Lung-Shen Lin, Taipei (TW); Li-Yen Edward Chang, Taipei (TW)

(73) Assignee: Development Center for Biotechnology, Taipei (TW)

( * ) Notice: Subject to any disclaimer, the term of this patent is extended or adjusted under 35 U.S.C. 154(b) by 0 days.

(21) Appl. No.: 09/684,546

(22) Filed: Oct. 6, 2000

(30) Foreign Application Priority Data

Mar. 6, 2000  (TW) ........................ 89103937 A

(51) Int. Cl.[7] ........................ A61K 39/12; C12N 15/00; C12P 21/06
(52) U.S. Cl. ................. 424/199.1; 424/815; 435/320.1; 435/69.1
(58) Field of Search ............... 424/216.1, 199.1, 424/186.1, 815; 435/320.1, 69.1; 536/23.72

(56) References Cited

U.S. PATENT DOCUMENTS 6,200,576 B1 * 3/2001 Hwong et al. ........... 424/216.1

FOREIGN PATENT DOCUMENTS

EP    0982403 A1 *  1/2000

OTHER PUBLICATIONS

Hagan and Bruner's Microbiology and Infectious Diseases of Domestic Animals, Eighth Edition. Ed. J.F. Timoney etal, Comstock Publishing Associates, Ithaca, NY, pp. 674–676, 1988.*

Zhang et al., "Molecular evolution of swine . . . ," Journal of General Virology, 80:639–651, 1999.

Inoue et al., "Production of infectious swine . . . ," Journal of General Virology, 71:1835–1838, 1990.

Jiménez–Clavero et al., "Immune Recognition of Swine . . . ," Virology, 270:76–83, 2000.

Frolov et al., "Alphavirus–based expression . . . ," Proc. Natl. Acad. Sci, USA, 93:11371–11377, 1996.

Berglund et al.,"Enhancing immune responses . . . ," Nature Biotechnology, 16:562–565, 1998.

Hariharan et al., "DNA Immunization against . . . ," Journal of Virology, 72(2):950–958, 1998.

Inoue et al., "Viruses produced from . . . ," Archives of Virology, 143:1055–1062, 1998.

Kanno et al., "Mapping the Genetic . . . ," Journal of Virology, 73(4):2710–2716, 1999.

Inoue et al., "The Complete Nucleotide . . . ," J. gen. Virol, 70:919–934, 1989.

Martino et al., "The Coxsackie–Adenovirus Receptor . . . ," Virology, 271:99–108, 2000.

* cited by examiner

Primary Examiner—Ali R. Salimi
(74) Attorney, Agent, or Firm—Fish & Richardson P.C.

(57) ABSTRACT

The invention relates to nucleic acids containing a nucleotide sequence encoding a polypeptide, the polypeptide having (1) the P2 and P3 regions of a swine vesicular disease virus polyprotein, and (2) an amino acid sequence heterologous to the polyprotein. The invention also includes methods of preparing such nucleic acids (e.g., RNA or DNA expression vectors) and methods of using such nucleic acids to express RNA or protein.

1 Claim, 4 Drawing Sheets

FIG. 2

SWINE VESICULAR DISEASE VIRUS EXPRESSION VECTORS

BACKGROUND OF THE INVENTION

Swine vesicular disease virus (SVDV) is an enterovirus of the picornaviridae family and causes swine vesicular disease. The mature virus particle contains (+)-strand polyadenylated RNA generally about 7,400 bases in length. Thus, the SVDV genome is also a functional mRNA, which is composed of P-1, P-2, and P-3 regions (FIG. 1). The entire viral genome contains only one open reading frame, from which a precursor polyprotein is generated. The polyprotein is cleaved into mature viral proteins by a virus-specific protease (see P2 region in FIG. 1). The P-1 region contains four viral structural proteins, VP-1, VP-2, VP-3, and VP-4 (also known as 1A, 1B, 1C, and 1D, respectively), which form the capsid of the virus. The P-2 region contains non-structural viral proteins 2A, 2B, and 2C; and the P-3 region contains non-structural proteins 3A, 3B, 3C, and 3D. As used herein, the P-1, P-2, and P-3 regions can refer to either the nucleotide sequences in these regions or the amino acid sequences encoded thereby.

During the virus life cycle, SVDV enters the cell, releases the genome into the cell, and translates viral proteins from the genomic mRNA. Using the viral RNA-dependent RNA polymerase, the virus produces (−)-strand RNA, which in turn serves as a template for the production of more (+)-strand RNA for translation or packaging into virions. Further details regarding SVDV virology can be found in Kanno et al., J. Virol. 73:2710–2716, 1999; Zhang et al., J. Gen. Virol. 80:639–651, 1999; and references cited therein.

SUMMARY OF THE INVENTION

The invention is based on the discovery that cloned SVDV genomes, in both RNA and DNA form, can be used as vectors for expressing heterologous RNA or protein. Particularly, it has been discovered that replacement of the P1 region of a SVDV genome with a relatively large heterologous nucleotide sequence is sufficient for expression of heterologous RNA and protein.

Accordingly, the invention features a nucleic acid (i.e., an RNA or DNA molecule) having a nucleotide sequence encoding a polypeptide, the polypeptide containing (1) the P2 and P3 regions of a swine vesicular disease virus polyprotein, and (2) a heterologous amino acid sequence.

A heterologous amino acid sequence can be 8, 10, 20, 50, 100, or 200 or more amino acids in length. In addition, a heterologous nucleotide sequence can be 22, 50, 100, 200, or 400 or more bases or base pairs in length. The term "heterologous" means that the amino acid or nucleotide sequence does not fully correspond to a genomic or polyprotein sequence of a naturally occurring SVDV. A "polyprotein" is the polypeptide produced by translation of a SVDV genome (e.g., a naturally occurring SVDV genome).

The nucleic acids of the invention can further include a promoter operably linked to the nucleotide sequence, i.e., the promoter is configured to transcribe an RNA encoded by the nucleotide sequence.

The invention also includes (1) an RNA molecule having a swine vesicular disease virus genome and a heterologous nucleotide sequence inserted into or replacing the P1 region of the genome, and (2) a swine vesicular disease virus whose genome contains a heterologous nucleotide sequence inserted into or replacing the P1 region of the genome.

Also included in the invention is a method of producing a swine vesicular disease virus expression vector by providing a DNA molecule having (1) a nucleotide sequence encoding the P2 and P3 regions of a swine vesicular disease virus polyprotein, and (2) a promoter operably linked to the nucleotide sequence; and inserting a heterologous nucleotide sequence into the DNA molecule, where transcription from the promoter results in an RNA comprising the nucleotide sequence encoding (a) the P2 and P3 regions and (b) the heterologous nucleotide sequence. The heterologous nucleotide sequence can encode a heterologous amino acid sequence, and the RNA can encode a fusion protein containing (1) the P2 and P3 regions and (2) the heterologous amino acid sequence. The method can further include transcribing (in vitro or in vivo) the RNA from the promoter to produce an RNA expression vector.

The invention also includes a kit for expression of a heterologous protein, the kit containing a nucleic acid having (1) a nucleotide sequence encoding the P2 and P3 regions of a swine vesicular disease virus polyprotein, and (2) a polylinker flanking the nucleotide sequence and configured for insertion of a heterologous nucleotide sequence. A "polylinker" is a nucleotide sequence having artificially introduced restriction endonuclease recognition sites, especially sites of five or more base pairs in length. A polylinker can be 10, 20, 50, or even 100 or more nucleotides in length, and can have a concentration of restriction endonuclease recognition sites of at least two per 10 base pairs, on average, for the entire length of the polylinker. The nucleic acid can further include a promoter operably linked to the nucleotide sequence, and the kit can further include a cell susceptible to infection by a SVDV.

Additionally, the invention features a method of expressing an RNA in a cell by introducing into a cell (e.g., MVPK porcine kidney cells) a DNA molecule having (1) a DNA sequence encoding an RNA molecule including (a) a nucleotide sequence encoding the P2 and P3 regions of a swine vesicular disease virus polyprotein, and (b) a heterologous nucleotide sequence, and (2) a promoter operably linked to the DNA sequence; and culturing the cell under conditions sufficient to transcribe the RNA from the promoter. Where the promoter is inducible, the cell is generally contacted with an inducer compound in a culture to transcribe the RNA. If no inducer is required for expression, standard tissue culture conditions are sufficient for expression of the RNA. As described above, the heterologous nucleotide sequence can encode a heterologous amino acid sequence.

If expression of fusion protein is desired, the method of expressing an RNA can include the additional step of translating the RNA to express a fusion protein having (1) the P2 and P3 regions and (2) the heterologous amino acid sequence. In many cases, only continued culturing of the cell is required for translation.

Also featured in the invention is a composition (e.g., a vaccine composition) containing a nucleic acid of the invention. Where the composition is intended to be a vaccine, the heterologous amino acid sequence would encode an antigen, such as a SVDV antigen, to produce a SVDV vaccine. Other antigens can include tumor antigens, viral antigens (e.g., that of HCV), bacterial antigens (e.g., that of a pathogenic *Escherichia coli*), and antigens of eukaryotic pathogens (e.g., of a yeast, mycoplasma, protist, fungus, or worm).

The nucleic acids and methods of the invention can be used as a new platform technology for expressing RNA and polypeptides. The relatively simple genomic structure and virus life cycle of SVDV allows for easy manipulation of genetic material and introduction of such material into cells. An exemplary SVDV suitable for use in the invention is the Taiwan Yu-Li strain, which is described in U.S. patent application Ser. No. 09/116,032, now allowed.

Other features or advantages of the present invention will be apparent from the following detailed description, and also from the claims.

BRIEF DESCRIPTION OF THE DRAWINGS

FIGS. 2 and 3 are schematic diagrams of the cloning procedure used to generate pCI(□ΔXbaI)/SVDV-T(XbaI) and pCI(□ΔXbaI)/SVDV(□ΔP1)/GFP, respectively.

DETAILED DESCRIPTION

Figure 1:
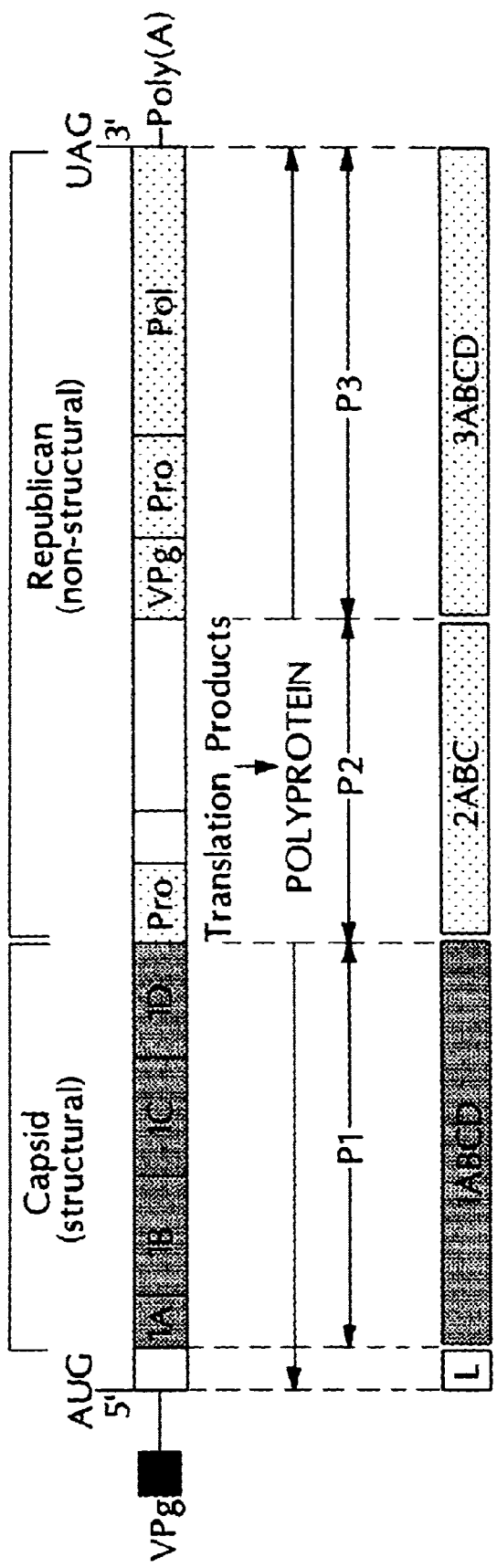
FIG. 1 is a schematic diagram of a SVDV genome or mRNA, and the mature viral proteins encoded therein.

The invention relates to a new viral expression system based on the SVDV genome and life cycle. SVDV nucleic acid sequences and virus clones are readily available. See, e.g., Zhang et al., J. Gen. Virol. 80:639–651, 1999, and references cited therein, as well as U.S. Ser. No. 09/116,032.

Without further elaboration, it is believed that one skilled in the art can, based on the above disclosure and the construction of SVDV expression vectors described below, utilize the present invention to its fullest extent. The following examples are to be construed as merely illustrative of how one skilled in the art can make and use SVDV vectors for expressing heterologous RNA and proteins, and are not limitative of the remainder of the disclosure in any way. All publications cited in this disclosure are hereby incorporated by reference.

EXAMPLES

Example 1

Full Length SVDV DNA Vector for Expression of Heterologous Sequences

Figure 2:
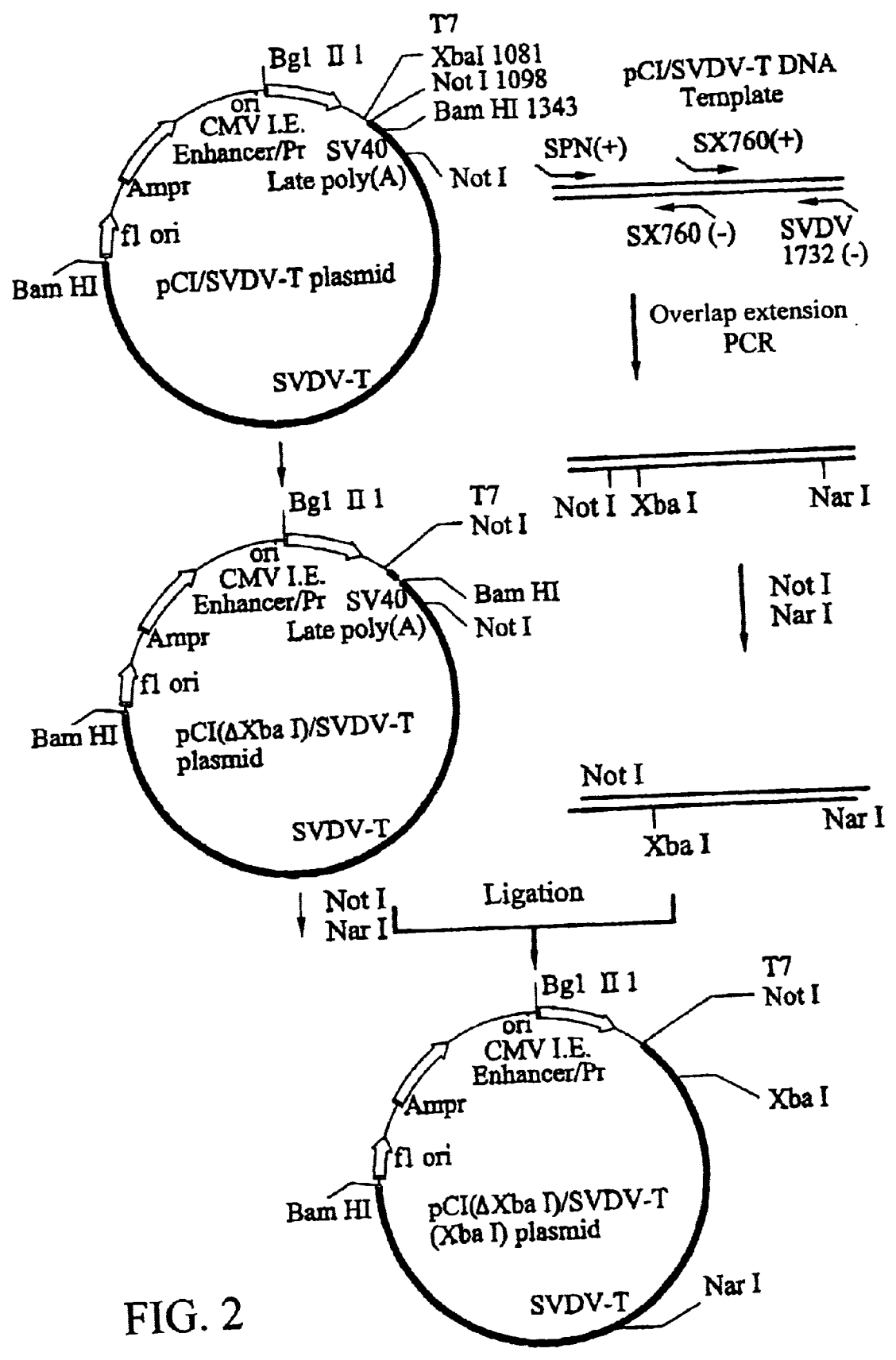

The pCI(□ΔXbaI)/SVDV-T(XbaI) vector was constructed as shown in FIG. 2, using pCI/SVDV-T as the starting material (U.S. Ser. No. 09/116,032). The XbaI site in the parent pCI vector was deleted, and another XbaI site was introduced into the SVDV cDNA at about position 760 bp (all numberings are as in U.S. Ser. No. 09/116,032), just upstream of the protein 1A coding sequence. Consequently, the new XbaI site, together with the NarI site at about position 3300 bp 0ust downstream of the protein 1D coding sequence) can be used to replace the P-1 region with a heterologous sequence. The specific procedure for constructing pCI(□ΔXbaI)/SVDV-T(XbaI) is described below.

The pCI/SVDV-T vector was treated with XbaI at 37° C. for 2 hours. After purification of the digestion products, both ends of the vector were blunted with 5 U/100 μl of pfu DNA polymerase at 72° C. for 1 hour, and ligated using T4 DNA ligase. The ligation products were used to transform DH5□α E. coli. The bacteria were grown, and the plasmid DNA purified from the bacteria. The purified vector was then digested with XbaI to confirm the identity of the plasmid. This plasmid deleted for the XbaI site was named pCI(□ΔXbaI)/SVDV-T (FIG. 2).

The 1,732 bp DNA fragment between the NotI and NarI sites in the pCI(□ΔXbaI)/SVDV-T was prepared using overlap extension PCR (FIG. 2). An XbaI site was inserted at about nucleotide position 760. The PCR-generated fragment was then used to replaced the corresponding NotI to NarI fragment in pCI(□ΔXbaI)/SVDV-T to produce pCI (□ΔXbaI)/SVDV-T(XbaI). The detailed procedure is described below and in FIG. 2.

pCI(□ΔbaI)/SVDV-was used as template, along with primers SPN(+), SX760(-), SX760(+), and SVDV1732(-). The primer sequences were:

SPN(+): CCGGGCGGCCGCTAATACGACTCACTA (SEQ ID NO:1)

SX760(-): CTTTTGTGTTGACTCTAGAGCTC-CCATTTTAAC (SEQ ID NO:2)

SX760(+): GTTAAAATGGGAGCTCTAGAGTCAA-CACAAAAG (SEQ ID NO:3)

SVDV1732(-): TTGCTTGCCGGCCAGACGCAGC-CCATT (SEQ ID NO:4)

The PCR solution contained of 10 μl of 10×ExTag buffer (TaKaRa), 8 μl of 2.5 mM each dNTP, 0.2 μg of each primer, 0.05 μg of template, and 2.5 U of ExTag (TaKaRa). Water was added to achieve a 100 μl volume. The PCR was performed at 94° C. for 1 minute; for 30 cycles of 94° C. for 30 seconds, 58° C. for 30 seconds, 72° C. for 1 minute; then at 72° C. for 3 minutes. The PCR product was analyzed using 0.8% agarose gel electrophoresis. A 780 bp DNA product was observed using SPN(+) and SX760(-), and a 980 bp DNA product was observed using SX760(+) and SVDV1732(-). The DNA fragments were digested with restriction endonuclease and purified for a second PCR reaction.

The second PCR reaction contained 0.1 mg each of the 780 bp and 980 bp fragments, 0.2 mg each of SPN(+) and SVDV1732 (-), 10 μl of 10×ExTag buffer, 8 μL of 2.5 mM each dNTP, 2.5 U of ExTag, and water to 100 μl total volume. The PCR was performed at 94° C. for 1 minute; for 30 cycles at 94° C. for 30 seconds, 60° C. for 1 minute, 72° C. for 2 minutes; and at 72° C. for 3 minutes. The PCR product was analyzed using 0.8% agarose gel electrophoresis. A 1.8 kb DNA product was clearly observed. The DNA fragment was purified and digested with NotI and NarI at 37° C. for 2 hours. After separation using 0.8% agarose gel electrophoresis, the DNA fragment was purified and stored at 4° C.

The pCI(□ΔXbaI)/SVDV-T vector was also digested with NotI and NarI at 37° C. for 2 hours. After separation using 0.8% agarose gel electrophoresis, the 8.0 kb linear DNA was purified and ligated to the 1.8 kb PCR product. The ligation was carried out at 16° C. for 30 minutes using T4 DNA ligase. DH5□α bacteria were transformed with the ligation reaction and grown. Clones which yielded a single full length linear fragment after digestion with XbaI were sequenced to confirm the identity of plasmid pCI(□ΔXbaI)/ SVDV-T(XbaI).

Figure 3:
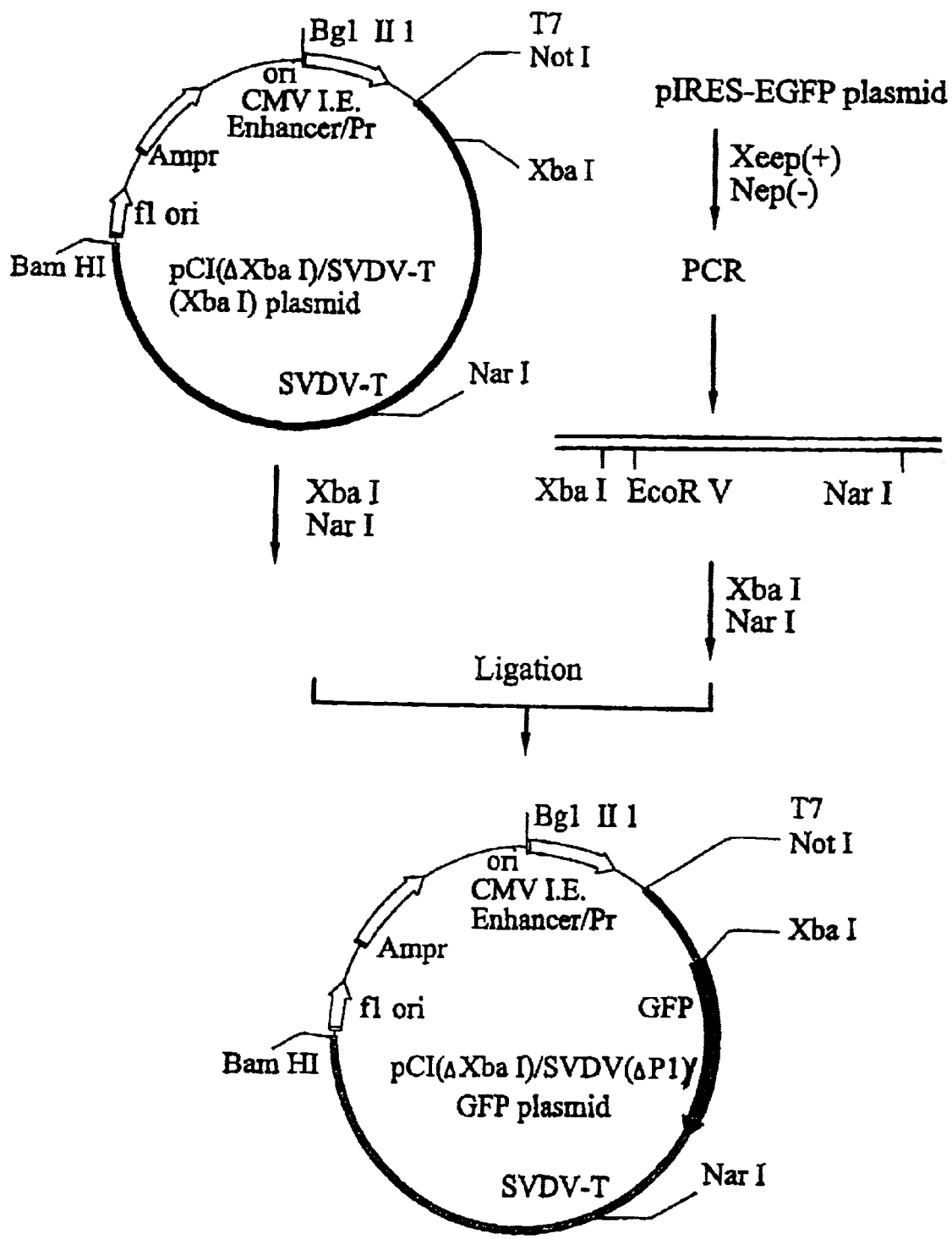

The pCI(□ΔXbaI)/SVDV-T(□ΔP1)/GFP expression vector was constructed as shown in FIG. 3. The purpose of this construct was to determine whether the SVDV DNA vector can express heterologous proteins. The green fluorescence protein (GFP) gene having XbaI and NarI restriction sites on the 5' and 3' ends, respectively, was prepared by PCR. The GFP fragment was then used to replace the XbaI to NarI fragment of pCI(□ΔXbaI)/SVDV-T(XbaI). In other words, the P-1 region of the SVDV genome was replaced with a GFP coding sequence. The detailed procedure is described below.

pIRES-EGFP (Clontech) was used as template for PCR, utilizing PCR Primers XEEP(+) (TTCTAGATATCG TGAGCAAGGGCGAGGAGCTGTTCACC [SEQ ID NO:5]) and NEP(−) (TTTGGCGCCAGTGGT CTTGTA-CAGCTCGTCCATGCCGAAAGT [SEQ ID NO:6]). The PCR reaction contained 10 µl of 10×ExTag buffer, 8 µl of 2.5 mM each dNTP, 0.2 µg each primer, 0.05 µg of template, 2.5 U of ExTag, and water to 100 µl total volume. PCR was performed at 94° C. for 30 seconds; and for 30 cycles of 55° C. for 40 seconds, 72° C. for 45 seconds. The PCR product was analyzed using 0.8% agarose gel electrophoresis. A 0.7 kb DNA product was observed. The 0.7 kb DNA fragment was purified and digested with XbaI and NarI at 37° C. for 2 hours. After separating the DNA fragment using 0.8% agarose gel electrophoresis, the 0.7 kb product was purified and stored at 4° C.

pCI(□ΔXbaI)/SVDV-T(XbaI) vector was digested with XbaI and NarI at 37° C. for 2 hours. After separating the vector fragment using 0.8% agarose gel electrophoresis, the 9.5 kb linear DNA was purified and ligated to the 0.7 kb GFP fragment. The ligation was carried out at 16° C. for 30 minutes using T4 DNA ligase. DH5□α bacteria were transformed with the ligated products and grown clones containing only one cutting site for EcoRV was selected and sequenced to the confirm identity of the new SVDV/GFP expression vector pCI(□ΔXbaI)/SVDV-T(□ΔP1)/GFP.

Example 2

Preparation of SVDV RNA Vector pCI(□ΔXbaI)/SVDV-T(□ΔP1)/GFP vector was linearized using BamHI at 37° C. for 2 hour. The linear DNA was separated using 0.8% agarose gel electrophoresis. The 10 kb DNA fragment was purified and stored at 4° C., then used as a template for in vitro transcription using T7 RNA polymerase. The detailed procedure is described below.

The transcription reaction contained 20 µl of 5×transcription buffer (Promega), 10 µl 100 mM DTT, 100 U of RNasin (Gibco-BRL), 2 µl of 25 mM rNTP mixture (Promega), 50 U of T7 RNA polymerase (Promega), 2 µg of template, and water to 100 µl total volume. After incubation at 37° C. for 1 hour, 10 U of DNaseI (Gibco-BRL) was added to the reaction, and the incubation continued at 37° C. for 10 minutes. The reaction was extracted with phenol/chloroform. The extracted RNA was precipitated with ethanol, dissolving in water, and analyzed using 1.0% agarose gel electrophoresis. The agarose gel indicated the presence of RNA of about 5.5 kb and provided no evidence of residual pCI(□ΔXbaI)/SVDV(□ΔP1)/GFP vector.

Example 3

Expression of Heterologous Protein Using SVDV Vectors

About 1–2×10⁵ MVPK porcine kidney cells were seeded in each well of a 6-well microplate and cultured in 3 ml of MEM medium supplemented with fetal bovine serum to 5%, at 37° C. in a 5% $CO2_2$ incubator. When the cells were grown to about 80% confluency, the following solutions were prepared. Solution A: 1 µg of pCI(□ΔXbaI)/SVDV (□ΔP1)/GFP or 0.5 µg of the chimeric RNA produced in Example 2 was added to 100 µl of OPTI-MEM (Gibco-BRL). Solution B: 20 µl of lipofectin (Gibco-BRL) was dissolved in 100 µl of OPTI-MEM. Solutions A and B were mixed together and incubated at room temperature for 15 minutes.

The MVPK cells were washed twice with 1×PBS buffer. About 0.8 ml of OPTI-MEM was added to each well, followed with the addition of the A/B mixture. The transfected MVPK cells were incubated at 37° C. for 6 hours and then washed with PBS. Three milliliters of MEM supplemented with fetal bovine serum to 5% was added to the washed cells, and the cells incubated at 37° C. After 16 hours growth, MVPK cells were observed under a fluorescent microscope. MVPK cells transfected with either the chimeric RNA or the DNA vector showed abundant fluorescence in individual cells, when compared to control cells transfected with the parent SVDV vector without GPF. The fluorescence in RNA-transfected cells appeared to be stronger than in DNA-transfected cells.

Figure 4:
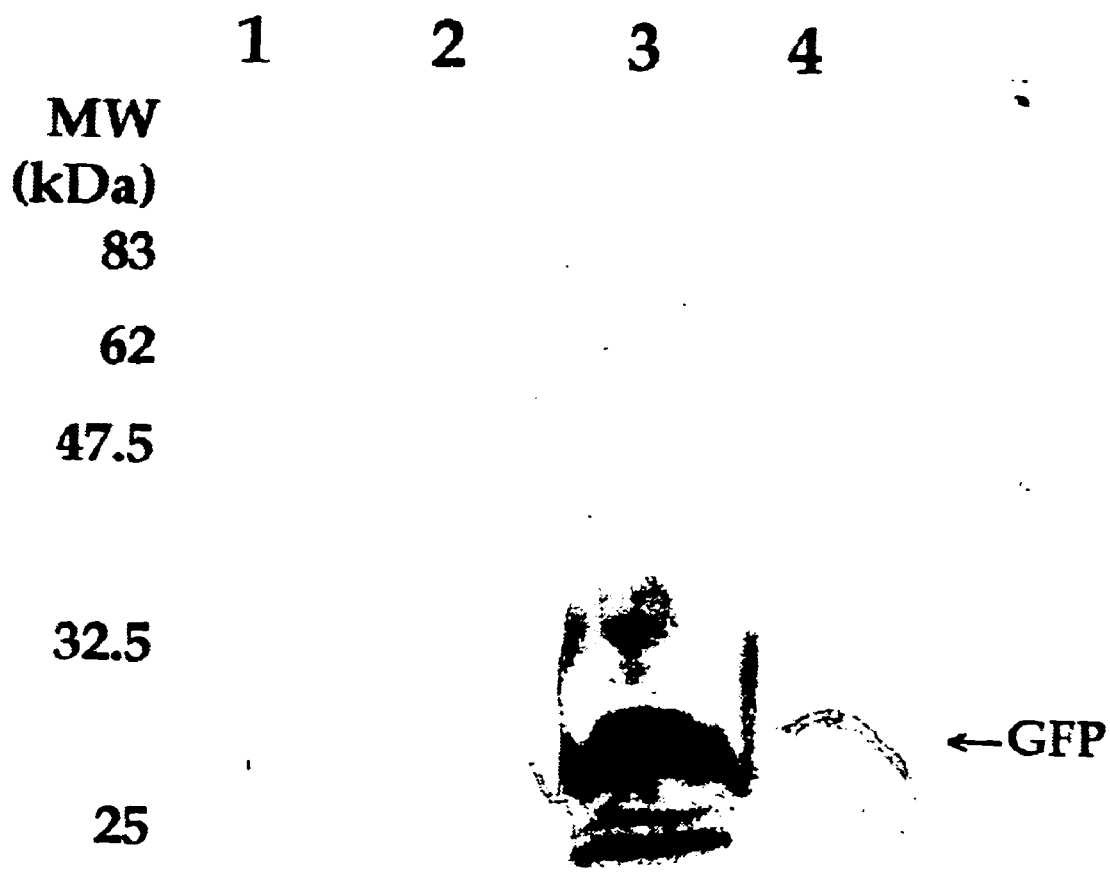
FIG. 4 is a photograph of a Western blot showing the GFP expressed after transfection of cells with a SVDV vector of the invention. Lane 1: protein standards. Lane 2: cells transfected with SVDV control vector (without GFP gene). Lane 3: cells transfected with pCI(□ΔXbaI)/SVDV(□ΔP1)/ GFP-derived RNA. Lane 4: Cells transfected with pCI (□ΔXbaI)/SVDV(□ΔP1)/GFP DNA.

In addition, the expression of GFP was evaluated using Western blotting and an anti-GFP antibody (Clontech). The Western blot results (FIG. 4) were similar to the fluorescence results. Both cells receiving the DNA or the RNA vector expressed GFP, though again RNA-transfected cells appear to produce more GFP than DNA-transfected cells. The Western blots also confirmed that GFP was cleaved from the SVDV polyprotein. These results indicate that a heterologous polypeptide can be expressed using either RNA or DNA SVDV expression vectors.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention. For example, SVDV genomes containing a P-1 sequence replacement can be packaged into virions using cells that stably express SVDV structural proteins. Such viral vectors would be expected to infect cells and express whatever heterologous sequences are present in P-1.

What is claimed is:

1. An expression vector consisting of the nucleotide sequence of pCI(□ΔXbaI)/SVDV-T(XbaI), excluding any sequence that encodes any P-1 region.

* * * * *

SEQUENCE LISTING

<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: primer

<400> SEQUENCE: 1
ccgggcggcc gctaatacga ctcacta

```
<210> SEQ ID NO 2
<211> LENGTH: 33
<212> TYPE: DNA
<213> ORGANISM: Artificial Sequence
<220> FEATURE:
<223> OTHER INFORMATION: primer

<400> SEQUENCE: 2
cttttgtgtt gactctagag ctcccatttt aac                                33

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
gttaaaatgg gagctctaga gtcaacacaa aag                                33

<210> SEQ ID NO 4
<211> LENGTH: 27
<212> TYPE: DNA
<213> ORGANISM: Artificial Sequence
<220> FEATURE:
<223> OTHER INFORMATION: primer

<400> SEQUENCE: 4
ttgcttgccg gccagacgca gcccatt                                       27

<210> SEQ ID NO 5
<211> LENGTH: 38
<212> TYPE: DNA
<213> ORGANISM: Artificial Sequence
<220> FEATURE:
<223> OTHER INFORMATION: primer

<400> SEQUENCE: 5
ttctagatat cgtgagcaag ggcgaggagc tgttcacc                           38

<210> SEQ ID NO 6
<211> LENGTH: 42
<212> TYPE: DNA
<213> ORGANISM: Artificial Sequence
<220> FEATURE:
<223> OTHER INFORMATION: primer

<400> SEQUENCE: 6
tttggcgcca gtggtcttgt acagctcgtc catgccgaaa gt                      42
```